(12) United States Patent
Chung et al.

(10) Patent No.: US 11,596,591 B2
(45) Date of Patent: Mar. 7, 2023

(54) MANUFACTURING METHOD FOR COSMETIC COMPOSITION OF FUCOIDAN AND COSMETIC COMPOSITION COMPRISING LOW MOLECULAR WEIGHT FUCOIDAN USING THE SAME

(71) Applicant: MS Global Bio Co., Ltd, Busan (KR)

(72) Inventors: Nam Ock Chung, Busan (KR); In Deok Kim, Busan (KR); Hyeon Seong Jeong, Busan (KR)

(73) Assignee: MS Global Bio Co., Ltd, Busan (KR)

( * ) Notice: Subject to any disclaimer, the term of this patent is extended or adjusted under 35 U.S.C. 154(b) by 22 days.

(21) Appl. No.: 17/318,573

(22) Filed: May 12, 2021

(65) Prior Publication Data
US 2022/0313589 A1   Oct. 6, 2022

(30) Foreign Application Priority Data
Mar. 31, 2021 (KR) .......................... 10-2021-0041704

(51) Int. Cl.
| | |
|---|---|
| A61K 36/02 | (2006.01) |
| A61K 8/73 | (2006.01) |
| A61K 8/9711 | (2017.01) |
| A61Q 19/08 | (2006.01) |
| A61K 8/99 | (2017.01) |
| A61Q 19/00 | (2006.01) |

(52) U.S. Cl.
CPC .............. *A61K 8/73* (2013.01); *A61K 8/9711* (2017.08); *A61K 8/99* (2013.01); *A61Q 19/00* (2013.01); *A61Q 19/08* (2013.01); *A61K 2800/84* (2013.01); *A61K 2800/85* (2013.01)

(58) Field of Classification Search
CPC ................................................. A61K 2800/84
See application file for complete search history.

(56) References Cited

FOREIGN PATENT DOCUMENTS

| | | | |
|---|---|---|---|
| JP | 2000239301 A | * | 9/2000 |
| KR | 10-1375775 B1 | | 3/2014 |

OTHER PUBLICATIONS

Hanjabam et al (Bioactive Carbohydrates and Dietary Fibre 20 (2019)). (Year: 2019).*

* cited by examiner

*Primary Examiner* — Qiuwen Mi
(74) *Attorney, Agent, or Firm* — Paratus Law Group, PLLC

(57) ABSTRACT

A method for manufacturing a fucoidan cosmetic composition includes: washing mozuku to eliminate residual salt and impurities; adding citric acid to the washed mozuku and pulverizing the mozuku; adding water to the pulverized mozuku and performing reflux extraction to obtain a high molecular weight fucoidan; adding a neutralizing agent to the high molecular weight fucoidan for neutralization; adding diatomite to the neutralized high molecular weight fucoidan and causing a reaction for 30 minutes for deodorization; filtering the deodorized high molecular weight fucoidan to eliminate insoluble substances; adding a lactic acid bacterium to the high molecular weight fucoidan removed of the insoluble substances and causing fermentation to obtain a low molecular weight fucoidan; concentrating the purified low molecular weight fucoidan with a reduced pressure evaporator; and powdering the concentrated low molecular weight fucoidan through freeze drying.

4 Claims, 6 Drawing Sheets

MANUFACTURING METHOD FOR COSMETIC COMPOSITION OF FUCOIDAN AND COSMETIC COMPOSITION COMPRISING LOW MOLECULAR WEIGHT FUCOIDAN USING THE SAME

CROSS-REFERENCE TO RELATED APPLICATION

This application claims priority to and the benefit of Korean Patent Application No. 10-2021-0041704 filed on Mar. 31, 2021, which is hereby incorporated by reference in its entirety.

BACKGROUND

The present invention relates to a method for manufacturing a fucoidan cosmetic and an anti-aging and functional cosmetic using the same, and more particularly to a method for manufacturing a fucoidan cosmetic and an anti-aging and functional cosmetic using the same, which method involves performing acid hydrolysis to obtain fucoidan as an extract of Mozuku, adding lactic acid bacteria for fermentation to degrade the molecular weight of fucoidan indicator substances to a low molecular weight, and removing proteins, fats and ash to prepare highly purified fucoidan.

Although the production of seaweeds in Korea is increasing year by year, the seaweed products are dominantly made through primary processing and do not induce an active promotion of consumption as a high-functional product. As a solution to this problem, there have been suggested "high value-added seaweed products using bioengineering technology", the examples of which may include fucoidan, carrageenan, alginic acid, and so forth.

Fucoidan is a type of viscous water-soluble plant fiber abundantly contained between cells of brown algae. It contains esterified sulfuric acid of fucose as a main component and is known to have various physiological activities, such as offering anticancer effects, increasing immunity, providing antiviral, antibacterial or antioxidant effects, improving the cholesterol level, promoting liver functions, inhibiting an increase in blood sugar, suppressing blood coagulation, and providing anti-allergic and skin-moisturizing effects. Mozuku is one of the most popular brown algae in recent years and attracting attention as a raw material of a fucoidan because it contains fucoidan 10 times more than sea mustard or kelp.

Mozuku is distributed in the central and southern parts of the Pacific coast, the Seto Inland Sea, the Korean Sea coast, and the Southwest Islands, and collected from spring to summer. Yet, *Nemacystus decipiens* Kuckuck (Itomozuku), *Cladosiphon okamuranus* Tokida (Okinawa mozuku), and *Cladosiphon novae*-caledoniae kylin (Tonga mozuku) are mainly used as a raw material of edible and functional foods.

Mozuku contains evenly various minerals, including vitamins, calcium, manganese, iron, and zinc. It is particularly rich in dietary fiber called alginic acid, which captures and excretes cholesterol in the body and strengthens resistance to cancer cells. Further, mozuku contains selenium, which inhibits the activity of cancer cells, and vitamin E for stabilization of selenium, which is a big plus.

Furthermore, mozuku is a useful resource with high industrial potential, suggesting its various uses as a functional additive for foods and cosmetics, because it contains abundant nutrients necessary for increasing immunity against various diseases and maintaining human health, including a benefit of anti-cancer effects.

Domestic companies that produce fucoidan are importing all of mozuku as a raw material from Japan. Although various physiological activities are expected, mozuku is mostly discarded, and its industrial use is very insufficient. Accordingly, the present invention is to construct a manufacturing process of a high value-added basic cosmetic using a marine resource, mozuku, and provide a novel type of seaweed-based cosmetic technology with functionality.

PRIOR ART DOCUMENTATION

Patent Documentation (Patent Document 0001) KR No. 10-1375775

SUMMARY

The present invention is devised to solve the above-mentioned problems. It is an object of the present invention to provide a method for manufacturing a functional cosmetic from mozuku that is currently used only for food.

It is another object of the present invention to provide a method for an effective extraction of mozuku using acid hydrolysis in addition to hot water extraction.

The above objects of the present invention are not intended as a definition of the limits of the invention. The above and other objects of the invention will become apparent to those skilled in the art from the following description of embodiments.

In order to achieve the objects of the present invention, there is provided a method for manufacturing a fucoidan cosmetic composition that includes: (1) washing mozuku to eliminate residual salt and impurities; (2) adding citric acid to the washed mozuku and pulverizing the mozuku; (3) adding water to the pulverized mozuku and performing reflux extraction to obtain a high molecular weight fucoidan; (4) adding a neutralizing agent to the high molecular weight fucoidan for neutralization; (5) adding diatomite to the neutralized high molecular weight fucoidan and causing a reaction for 30 minutes for deodorization; (6) filtering the deodorized high molecular weight fucoidan to eliminate insoluble substances; (7) adding a lactic acid bacterium to the high molecular weight fucoidan removed of the insoluble substances and causing fermentation to obtain a low molecular weight fucoidan; (8) concentrating the purified low molecular weight fucoidan with a reduced pressure evaporator; and (9) powdering the concentrated low molecular weight fucoidan through freeze drying.

According to the technical solution, the present invention can increase skin moisturization using the hydrophilicity of the sulfate group, which is contained more in fucoidan than in any other brown algae.

Further, the present invention can degrade the molecular weight of fucoidan to a low molecular weight through a fucoidan extraction method and use the low molecular weight fucoidan to significantly increase the absorption of fucoidan as a raw material for cosmetics.

Further, the present invention provides a fomented mozuku extract as a biocompatible material to make an effect of moisturizing the body tissue, wrapping a wound to heal, and preventing inflammation.

Furthermore, the present invention contains fucoidan as a raw material to make an effect of inhibiting the production of IgE, which is the cause of allergic disease manifested by atopic dermatitis or the like, and relieving allergic symptoms.

DETAILED DESCRIPTION

The terminology used in this specification will be first briefly defined, and a detailed description will be given as to the present invention.

The terms used in this specification are selected as general terms that are currently widely used as possible while taking the functions of the present invention into consideration. But, this may vary depending on the intention of those skilled in the art, precedents, the advent of new technologies, and the like.

Therefore, the terms used in this specification should be defined based on the meaning of the terms and the entire contents of the present invention, not just the name of the terms.

Throughout the specification, unless specified otherwise, the words "include" or "including" will be understood to imply the inclusion of a stated component, but do not preclude the inclusion of one or more other components.

Hereinafter, embodiments of the present invention will be described in detail with reference to the accompanying drawings so that the present invention may be readily implemented by those skilled in the art. However, it is to be noted that the present invention is not limited to the embodiments but can be embodied in various other ways.

The specified details including the technical problem, the technical solution, and the effects of the present invention are included in the embodiments and drawings in the following description of the present invention. The advantages and features of the present invention and the method for achieving them will become more apparent from the following detailed description of the invention taken in conjunction with the accompanying drawings.

Hereinafter, the present invention will be described in further detail with reference to the accompanying drawings.

Figure 1:
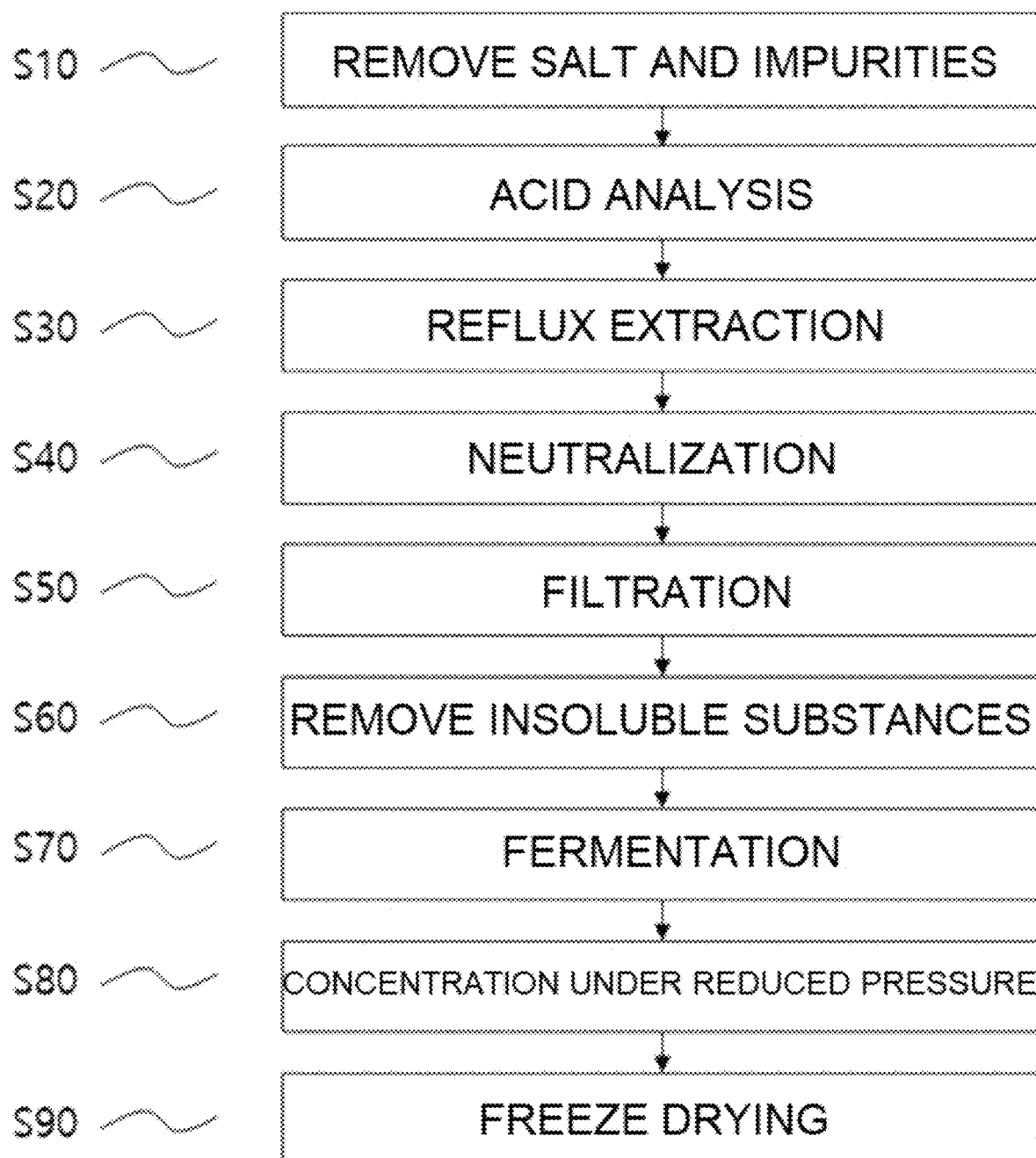
FIG. 1 is a flow chart showing a method for manufacturing a fucoidan cosmetic according to the present invention.

The present invention, a method for manufacturing a fucoidan cosmetic composition may be implemented in the following procedures, as shown in FIG. 1.

A first step S10 is washing mozuku to eliminate residual salt and impurities.

More specifically, the mozuku, which was dried or salted, was removed of residual salts and impurities by washing.

A second step S20 is adding citric acid to the washed mozuku and pulverizing the mozuku.

More specifically, in the second step S20, the citric acid was mixed in an amount of 0.08 part by weight with respect to one part by weight of the mozuku. If the content of the citric acid is less than 0.08 part by weight with respect to one part by weight of the mozuku, mozuku has a viscous form as high molecular weight polysaccharides, which has poor absorption and hence offers low efficacies when developed as a material for cosmetics or foods. If the content of the citric acid exceeds 0.08 part by weight with respect to one part by weight of the mozuku, mozuku is decomposed into monosaccharides, so it is unable to have functions inherent to fucoidan. It is therefore preferable to add the citric acid in an amount as defined above.

A third step S30 is adding water to the pulverized mozuku and performing reflux extraction to obtain a high molecular weight fucoidan.

More specifically, the reflux extraction of the third step S30 was preferably performed 60 to 100° C. under pressure of 0.1 to 2 kgf/cm$^2$ for 2 to 4 hours after mixing one part by weight of the water with respect to one part by weight of the pulverized mozuku. In the third step S30, the reflux extraction was performed at pH 2 to 3.

The conditions for the preparation of a mozuku-derived fucoidan extract were set so that an acid hydrolysis could be performed for a first process of producing a low molecular weight fucoidan in the second and third steps S20 and S30. In order to perform the acid hydrolysis, it is necessary to conduct an extraction under the strong-acid and high-temperature conditions. The strong-acid conditions involve a reaction using a highly erosive and volatile acid, which may cause safety problems at low pH values. The acidity conditions were defined in the range of pH 2-3.

As extremely high temperatures may cause problems such as explosion due to the high volatility of the strong acid, it is desirable to perform the reflux extraction at 60 to 100° C.

A fourth step S40 is adding a neutralizing agent to the high molecular weight fucoidan for neutralization. In order to minimize the continuing unnecessary acid hydrolysis with the acid after the reflux extraction of the third step S30, a neutralization process is performed in the following fourth step S40.

More specifically, the neutralizing agent was mixed in the almost same amount of the citric acid; preferably, 0.9 to 1 part by weight of the neutralizing agent was added with respect to one part by weight of the citric acid. The neutralizing agent may be any one selected from sodium hydroxide, calcium hydroxide, and potassium hydroxide. In the present invention, sodium hydroxide (NaOH) is preferably used to neutralize the acidic reaction conditions and maintain the pH 6.5 to 7.5.

A fifth step S50 is adding diatomite to the neutralized high molecular weight fucoidan and causing a reaction for 30 minutes for deodorization.

In order to eliminate the odor peculiar to the seaweed, diatomite is added to cause adsorption of pigments and flavors. The filtration process of the fifth step S50 can also be performed to achieve deodorization and sludge adsorption and improve chromaticity and turbidity.

A sixth step S60 is filtering the deodorized high molecular weight fucoidan to eliminate insoluble substances. More specifically, the sixth step S60 consists of a 6-1 step S61 of performing a filtration at 55 to 60° C. with a filter pressure to raise the filtration rate and filter out insoluble substances, and a 6-1 step S62 of using a multi-purpose purification system, ultrafiltration (UF) membrane, to eliminate heavy metals and salts posing a problem with seaweeds and obtain a high molecular weight fucoidan extract with high purity.

In order to solve an issue associated with a high salt content peculiar to the seaweed, the present invention uses a multi-purpose purification system, ultrafiltration (UF) membrane to achieve a removal of salts and impurities. The ultrafiltration (UF) can eliminate salts having a size less than 1 Kda, while the temperature is maintained at 60° C. or below to raise the filtration rate. The filtration with an inorganic membrane results in producing a mozuku-derived fucoidan extract with high purity.

A seventh step S70 is adding a lactic acid bacterium to the high molecular weight fucoidan removed of the insoluble substances and causing fermentation to degrade the fucoidan to a low molecular weight.

More specifically, the lactic acid bacterium of the seventh step S70 is preferably any one selected from the group consisting of *Lactobacillus delbrueckii* subsp. *Lactis* (KCTC 3034), *Lactobacillus plantarum* subsp. *Plantarum* (KCTC 3107), *Lactobacillus acidophilus* (KCTC 3145), *Streptococcus salivarius* subsp. *Thermophiles* (KCTC 5098), and *Lactobacillus casei*.

The *Lactobacillus* is a genus of bacteria that ferments saccharides to obtain energy and generates a large amount of lactic acids. Morphologically, *Lactobacillus* is a Gram-positive non-spore-forming *bacillus*, which exhibits polymorphism, and ranges in size from 0.5×1 μm to 0.9×11 μm, representing various types from short *Bacillus* to long *Bacillus*. This genus grows in an oxygen-free environment and produces lactic acids from various sugars. Low molecular weight effective substances increase the skin absorption rate and have excellent effects to soothe and restore the skin tired from various stresses in a short period of time. The *Streptococcus salivarius* subsp. *thermophiles* is selected as a lactic acid bacterium that has high anti-inflammatory and skin-whitening efficacies.

In addition, the seventh step S70 is preferably performed to achieve fermentation at 36 to 38° C. for 72 hours.

In order to establish the fermentation process using lactic acid bacteria in the seventh step S70, lactic acid bacteria in the genus of *Lactobacillus, Bifidobacterium, Lactococcus, Streptococcus,* or *Enterococcus* and several species of yeasts were inoculated at a concentration of 0.2% and then cultured for fermentation at 37° C. for 72 hours.

Table 1 presents the strains used in this experiment.

TABLE 1

| Strain name | Strain No. | Delivery form |
|---|---|---|
| *Lactobacillus delbrueckii* subsp. *lactis* | KCTC 3034 | Freeze dried ampoule/vial (general distribution) |
| *Lactobacillus plantarum* subsp. *Plantarum* | KCTC 3107 | |
| *Lactobacillus acidophilus* | KCTC 3145 | |
| *Streptococcus salivarius* subsp. *thermophiles* | KCTC 5098 | |
| *Lactobacillus casei* | KCTC 3109 | Actively growing culture (Actively growing culture distribution) |

Figure 2:
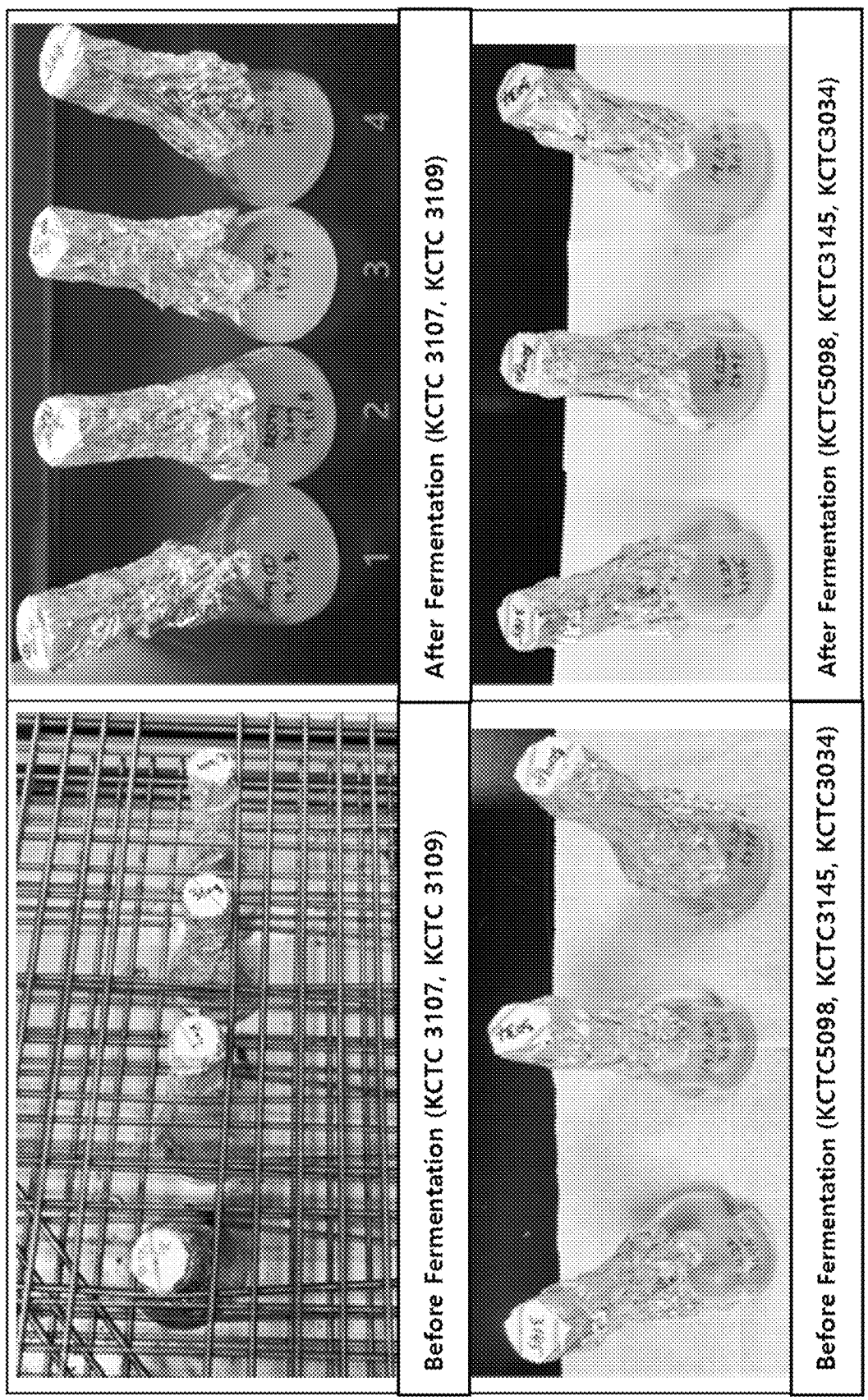
FIG. 2 is an image showing that screening of strains is performed for inoculation of the strain in the step (7).

The freeze-dried strains in the present invention were cultured on an MRS culture medium at 37° C. for 48 hours. Also, as shown in FIG. 2, low molecular weight strains were screened through a screening of strains for inoculation.

The mozuku-derived fucoidan extract is mainly composed of ash, lipids, carbohydrates, proteins, and a fucoidan indicator substance, which is a polysaccharide. Among the strains, a strain having excellent fermentation ability for the mozuku extract is selected and subjected to fermentation.

*Lactobacillus plantarum*, which has excellent fermentation ability for the mozuku-derived fucoidan extract, is a strain for intestinal health and skin health, such as improving skin itchiness and skin moisturization. *Lactobacillus casei* is a strain expected to remarkably degrade the molecular weight of a polysaccharide. These two lactic acid bacteria were added in an amount of 0.1% each and cultured at 37° C. for 72 hours for fermentation. The fermentation process was performed to degrade the indicator substance to a low molecular weight and eliminate proteins, fats, ash, and the like, resulting in producing fucoidan with high purity and increasing the yield of fucoidan.

After the completion of the fermentation in the seventh step S70, the fermented culture solution was heated up to 90 to 130° C. for 1 to 2 hours in an incubator to achieve sterilization and inactive microorganisms.

An eighth step S80 is concentrating the purified low molecular weight fucoidan with a reduced pressure evaporator. More specifically, the fermented culture solution was heated up to 90 to 130° C. for 1 to 2 hours in an incubator for sterilization and inactivation of microorganisms after the completion of the fermentation process of the seventh step S70 and then subjected to a concentration process under reduced pressure in the eighth step S80.

More specifically, the culture solution was concentrated through distillation using an evaporator at 40 to 45° C. under vacuum pressure of 0.06 Torr (0.029 mbar, 0.0029 kpa).

A ninth step S90 is powdering the concentrated low molecular weight fucoidan through freeze drying.

In the ninth step S90, the mozuku-derived fucoidan was formulated into a cosmetic material through a powdering process using a freeze drying system.

In order to establish the processes of the second and third steps S20 and S30, a general extraction, an ultrasonic extraction, a hot water extraction, or an acid hydrolysis extraction was performed. The solvents used for extraction were purified water and ethanol, and the extraction time was varied as 2, 4, 6, and 24 hours. According to this experiment, it was possible to establish the decomposition and degradation of algae-derived viscous polysaccharides to a low molecular weight and to eliminate the odor of marine algae generated during the processing of marine algae by filtration, deodorization, and removal of insoluble substances in the step subsequent to the second and third steps S20 and S30. It was also possible to determine the production yield for checking whether it was suitable for mass production.

The following Table 2 presents the extraction conditions according to the process design of the second and third steps S20 and S30.

TABLE 2

| Extraction conditions | Solvents | Extraction time range | Comments |
|---|---|---|---|
| General extraction (room temp.) | Purified water, ethanol | 4, 6, 12 hours | Extraction by time and solvent at room temp. |
| Ultrasonic extraction | Purified water, ethanol | 15, 30, 60 minutes | Extraction of active ingredients by physical force at room temperature |
| Hot water extraction | Purified water | 2, 4, 6 hours | Extraction of active ingredients of original product itself |

TABLE 2-continued

| Extraction conditions | Solvents | Extraction time range | Comments |
|---|---|---|---|
| Acid hydrolysis extraction | Purified water, citric acid (1-5%) | 2, 4, 6 hours | Extraction under acidic conditions using citric acid as acid hydrolysis conditions |

In the above process, a filtration was performed in order to eliminate the residue of mozuku. The process under various extraction conditions was explored to manufacture a low molecular weight fucoidan extract by extraction conditions.

The general extraction (at room temperature) yields a product, which is not suitable for use as a raw material for cosmetics due to its high viscosity. The ultrasonic extraction requires a high cost of the pretreatment process and a high operating cost and poses a limit on the maximum processing capacity. The hot water extraction preserves the color and odor peculiar to marine algae and the physiological activities of marine algae in the polymer form, so an additional extraction with degradation to a low molecular weight is necessary for the sake of absorption into the body. Degradation to a low molecular weight is performed using the acid hydrolysis method of the present invention as a means to reducing high production cost and maximizing the production efficiency for large-scale industrialization, and degradation to an ultra-low molecular weight is performed using an additional fermentation process to increase skin absorption of the product.

The content of fucose was measured in order to determine the purity index of the fucoidan prepared in the present invention.

Fucose, which composes fucoidan, is an indicator material that is attracting attention as a next-generation biomaterial due to its stronger anti-cancer, anti-inflammatory, and immune-boosting effects. It has an excellent effect of strengthening cells in the body, and not only protects the skin from harmful substances such as fine dust, but also fundamentally improves skin immunity. Therefore, the content of the indicator material, fucose was measured before and after the fermentation process.

[1] Analysis Conditions
Instrument: SHIMADZU HPLC, NH2P-50 Comumn 250*4.6 mm
Detector: RI Detector
Column oven temperature: 30° C.
Flow rate: 1.0 mL/min
Injection volume: 3 uL
Mobile phase: Idocratic, 250 mM $H_3PO_4$: Acetonitrile: 20:
Sample retreatment: Place 2 g of the sample into a round-bottom flask→Add 20 mL of 2M TFA and perform hydrolysis for 4 hours→Adjust pH to 7-8→Pass through 0.45 um syringe filter→HPLC analysis (2) Result Analysis
After fermentation, fucose as an indicator of the fucoidan of the mozuku-derived fucoidan powder increased by 22.9%, so the fucose content was higher than before the technical development. Such a high fucose content was applied to develop a cosmetic composition with high functionality.

An effectiveness analysis was performed as follows for the fucoidan produced by the manufacturing method for fucoidan cosmetic composition according to the present invention:

(A) Analysis of inhibitory effect against proliferation of cancer cells: MTT assay
(B) Verification of whitening effect of active ingredient: tyrosinase activity assay
(C) Evaluation of skin moisturizing effect, skin irritation test: inspection of skin conditions, such as moisture content, percutaneous moisture loss, or dead skin.

A. Analysis of Inhibitory Effect Against Proliferation of Cancer Cells: MTT Assay As a scientific and efficient safety evaluation method in the safety evaluation of cosmetics, toxicity evaluation was performed according to the KFDA guidelines. It was requested to perform a cytotoxicity evaluation by evaluating the activity of living cells as an index determining the total activity of cell population (the ability of a dehydrogenase of intracellular mitochondria to reduce the biological dye, MTT(3-(4,5-dimethyl thiazol-2-yl)-2,5-diphenyltetrazolium bromide, thiazolyl blue).

(1) Test object: Human keratinocytes cell line, HaCaT cells (2) Test method: Human keratinocytes cell line, HaCaT cells were used in the experiment for the in-vitro cytotoxicity test of the test substance, mozuku-derived fucoidan extract. The test substance was applied to the human keratinocytes cell line for 24 hours and measured in regards to the cytotoxicity. The measurements were analyzed in comparison to the control group to evaluate the cell viability.

Figure 3:
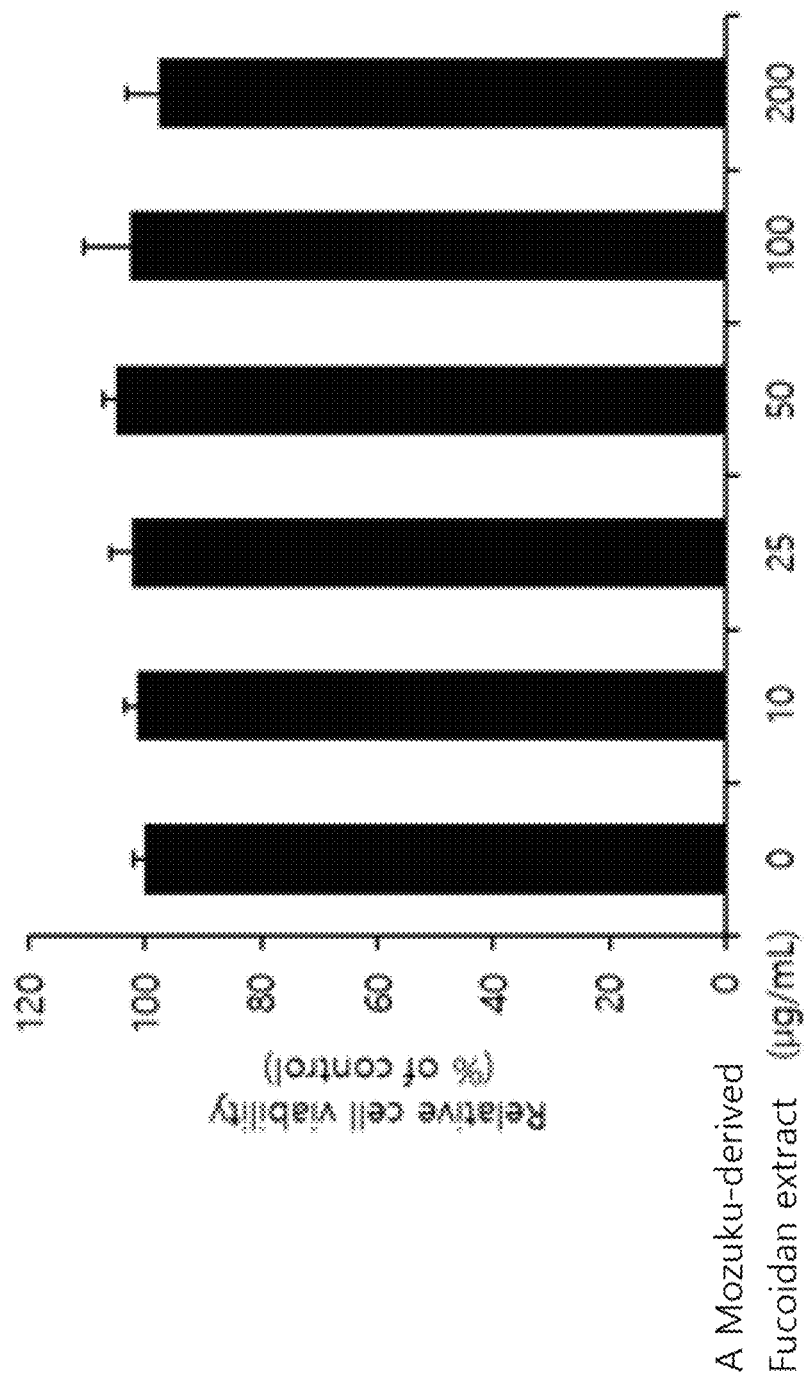
FIG. 3 is a graph showing the cell viability of human keratinocyte line (HaCaT cells) measured by performing an evaluation of toxicity of the fucoidan extract prepared by the present invention.

(3) Test results: The test substance commissioned by MS Global Bio Corp., Ltd., mozuku-derived fucoidan extract was applied at a concentration of 200 μg/mL or less, that is, 10, 25, 50, 100, or 200 μg/mL to the human keratinocytes cell line for an in-vitro cytotoxicity test. According to the test results, the cell viability was 101.31±2.31%, 102.37±3.50%, 105.04±2.08%, 102.73±7.89%, and 97.69±5.64% at respective concentrations with respect to the negative control, as shown in FIG. 3, revealing that there was no reduction of the cell viability.

(4) Conclusion: The Korea Institute of Dermatological Sciences conducted a cytotoxicity test of the test substance, mozuku-derived fucoidan extract on the human keratinocytes cell line as commissioned by MS Global Bio Corp., Ltd.

According to the evaluation results, when the test substance commissioned by MS Global Bio Corp., Ltd., mozuku-derived fucoidan extract was used at a concentration of 200 μg/mL or less, that is, 10, 25, 50, 100, or 200 μg/mL, the cell viability of the human keratinocytes cell line was 101.31±2.31%, 102.37±3.50%, 105.04±2.08%, 102.73±7.89%, and 97.69±5.64% at respective concentrations of the test substance with respect to the negative control, showing that there was no reduction of the cell viability (P>0.05).

Accordingly, the human keratinocytes cell line treated with the test substance commissioned by MS Global Bio Corp., Ltd., mozuku-derived fucoidan extract at a concentration of 200 μg/mL or less, that is, 10, 25, 50, 100, or 200 μg/mL showed no significant reduction of cell viability with respect to the negative control group. It was concluded from the results that the mozuku-derived fucoidan extract at a concentration of 200 μg/mL or less made no significant difference in cell viability and hence had no cytotoxicity to the human keratinocytes cell line.

B. Verification of Whitening Effect of Active Ingredient: Tyrosinase Activity Assay An in-vitro tyrosinase inhibition assay was used to determine whether the whitening ingredients were directly affecting the regulation of the tyrosinase activity (using tyrosine as a substrate). The ingredients with a whitening effect mainly have a mechanism of action that inhibits some processes in the melanin biosynthetic pathway in vivo, which is the initial process in which tyrosinase is involved in the most important process in the synthetic pathway. Most of the whitening ingredients inhibit the activity of tyrosinase and reduce the production of melanin in the skin, resulting in offering a skin whitening effect. A test analysis was requested according to the index criteria of the KFDA's whitening efficacy evaluation.

(1) Test method: For an in-vitro tyrosinase inhibition test of the test substance, mozuku-derived fucoidan extract, the tyrosinase inhibitory ability was measured using an in-vitro tyrosinase inhibition assay. The measurements were subjected to a comparative analysis with a negative control to evaluate the tyrosinase inhibition rate against the reaction of the substrate L-tyrosine.

(2) The evaluation of the in-vitro tyrosinase inhibition ability was performed by determining the degree of the inhibitory effect against tyrosinase involved in the melanin synthesis process. The tyrosinase inhibitory effect of the test substance was evaluated by measuring the absorbance of DOPAchrome produced from the substrate L-tyrosine by the enzymatic reaction of tyrosinase. A test substance diluted to a defined concentration and 1000 U/mL mushroom tyrosinase (Sigma Aldrich) were distributed to a 96-well plate, and a 50 mM potassium phosphate buffer (2 mM L-tyrosine dissolved at a defined pH) (Sigma Aldrich) was further added to cause a reaction at 37° C. for 30 minutes. A microplate reader system (SpectraMax® i3x Multi Mode Detection Platform Molecular Devices, USA) was used to measure the absorbance at 475 nm. The positive control in the in-vitro tyrosinase inhibition test was arbutin (200 μM). The measurements were presented as a standard deviation of the mean value from the three independent experiments. As determined by the Student's t test, $P<0.05$ was considered statistically significant. The in-vitro tyrosinase inhibition activity against the substrate L-tyrosine was calculated according to the following equation:

Tyrosinase inhibition activity=$[1-(A1-A3/A0-A2)] \times 100$

Figure 4:
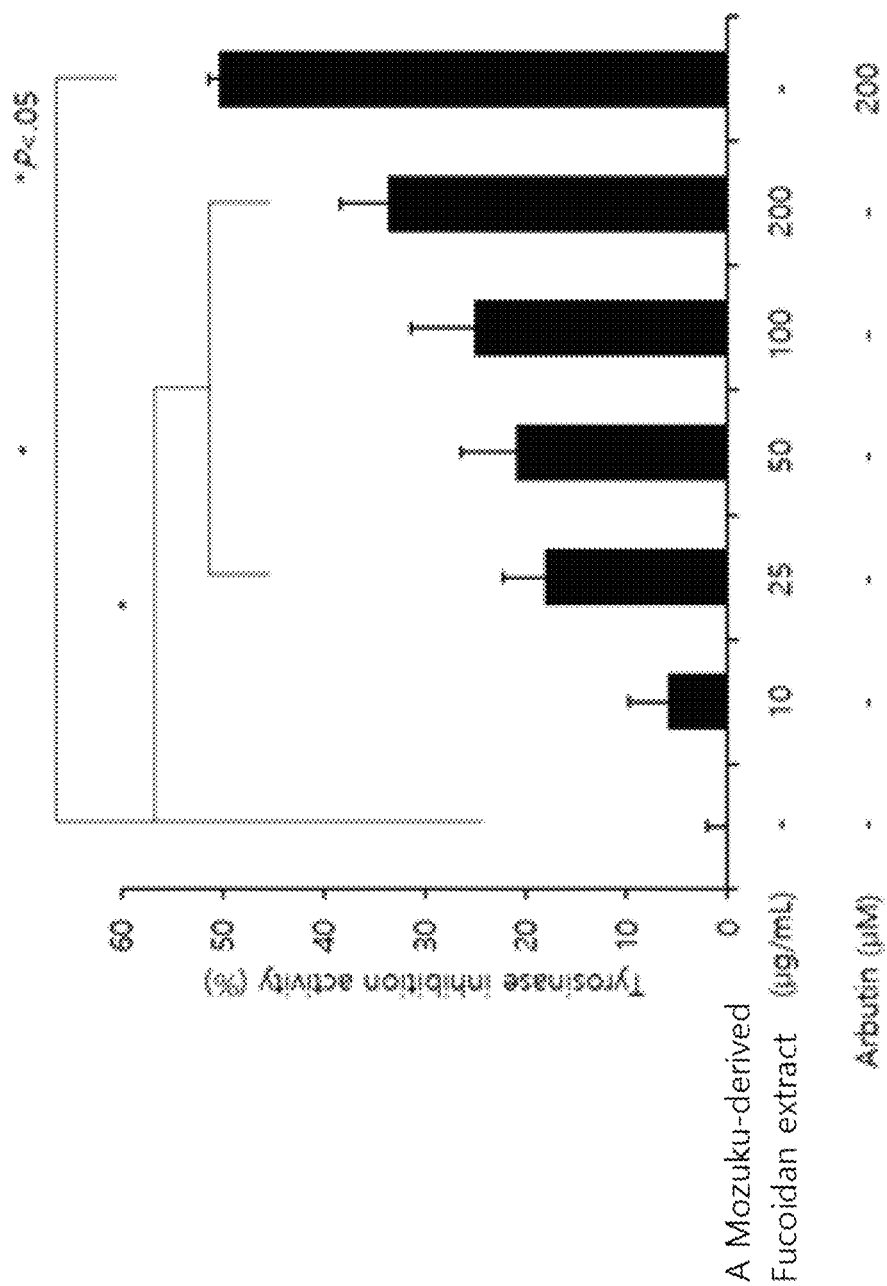
FIG. 4 is a graph showing the tyrosinase inhibitory activity with L tyrosine measured by a test for the tyrosinase inhibitory activities of the fucoidan extract prepared by the present invention.

A0: Absorbance of tyrosinase solution without sample
A1: Absorbance of tyrosinase solution with sample
A2: Absorbance of blank solution without tyrosinase solution and sample
A3: Absorbance of sample without tyrosinase solution (3) Test results: The change in the in-vitro tyrosinase activity was measured in the presence of the mozuku-derived fucoidan extract at a concentration of 200 μg/mL or less, that is, 10, 25, 50, 100, or 200 μg/mL. As shown in FIG. 4, the tyrosinase inhibitory activity against L-tyrosine was increased as 5.89±3.88%, 18.12±4.04%, 20.91±5.43%, 25.03±6.39%, and 33.71±4.61% with respect to the negative control at respective concentrations of the fucoidan extract. When using 200 μM arbutin as the positive control, the tyrosinase inhibition activity against L-tyrosine increased to 50.47±0.95% with respect to the negative control (P<0.05).

(4) Conclusion: The Korea Institute of Dermatological Sciences conducted an in-vitro tyrosinase inhibition test of the test substance, mozuku-derived fucoidan extract, as commissioned by MS Global Bio Corp., Ltd.

The test substance provided by MS Global Bio Corp., Ltd., mozuku-derived fucoidan extract was measured in regards to the tyrosinase inhibition activity against L-tyrosine at a concentration of 200 μg/mL or less, that is, 10, 25, 50, 100, or 200 μg/mL. According to the measurement results, the tyrosinase inhibitory activity against L-tyrosine was increased as 5.89±3.88%, 18.12±4.04%, 20.91±5.43%, 25.03±6.39%, and 33.71±4.61% with respect to the negative control at respective concentrations of the fucoidan extract. When using 200 μM arbutin as the positive control, the tyrosinase inhibition activity against L-tyrosine increased to 50.47±0.95% with respect to the negative control (P<0.05).

Accordingly, when the test substance commissioned by MS Global Bio Corp., Ltd., mozuku-derived fucoidan extract was used at a concentration of 200 μg/mL or less, that is, 10, 25, 50, 100, or 200 μg/mL, the tyrosinase inhibition activity against L-tyrosine increased to 33.71±4.61% at maximum with respect to the negative control. It was considered from the results that the mozuku-derived fucoidan extract at a concentration of 200 μg/mL or less inhibited tyrosinase from producing DOPA chrome and hence helped inhibit the in-vitro tyrosinase activity.

A facial mask was manufactured using the manufacturing method for fucoidan cosmetic composition according to the present invention. The composition of the facial mask was as given in the following Table 3.

TABLE 3

| Ingredients | Main functions | Materials | Contents |
| --- | --- | --- | --- |
| Purified water | Supplies moisture and functions as another hydrophilic solvent | Ion-exchange water | To 100 |
| Functional extract | Improves wrinkles, skin whitening and moisturization, and relieves inflammation | Adenosine, niacinamide, mozuku extract (5%), Centella extract | ~10% |
| Moisturizer | Helps skin moisturization and supplies moisture | Glycerin, butylene glycol, hyaluronic acid, arginine | ~15% |
| Emulsifier | Makes insoluble ingredients soluble | Polysorbate 80 | ~1% |
| Skin conditioner | Helps skin moisturization, smoothing and regeneration, and relieves inflammation | Betaine, aloe vera leaf extract, beta glucan, rosemary leaf extract, green tea leaf extract, noni fruit juice, macadamia nut oil, white willow bark extract, cinnamon bark extract, oregano leaf extract, cypress leaf extract, ethylhexyl glycerin | ~20% |
| Thickener | Increases viscosity of aqueous solution | Carbomer, hydroxyethyl cellulose | ~0.5% |
| Sequestering agent | Prevents metal components linking together | Di-EDTA | ~0.5% |
| Fragrance | Provides its own fragrant aroma | Fragrance | ~0.5% |

Each test subject was asked to evaluate the facial mask sheet in regards to skin sensitivity and feeling of use by sheet material and size by comparing before and after application of the facial mask.

TABLE 4

| Test name | Items | Score | Average | Comments |
| --- | --- | --- | --- | --- |
| Sensory test for fucoidan | Convenience | 4.0 | 4.3 | Feels light and easy to take out and use |

TABLE 4-continued

| Test name | Items | Score | Average | Comments |
|---|---|---|---|---|
| mask sheet in use | Fragrance | 4.2 | | Feels comfortable with delicate scent |
| | Absorption | 3.9 | | Good absorption |
| | Stickiness | 4.4 | | Almost no stickiness |
| | Skin irritations | 4.6 | | No skin irritations |
| | Feeling after use | 4.2 | | Moist and soft |
| | Adhesion to skin | 4.5 | | Good sheet adhesion and shrinkage to make skin moisturized |
| | Moisturization | 4.8 | | Excellent for moisturization |

In addition, a test for hazardous substances related to the fucoidan facial mask was performed. OATC Inc. was asked to inspect the hazardous substances of the facial mask formulation containing the mozuku-derived fucoidan extract. The inspection items were pH, lead, nickel, mercury, cadmium, and arsenic. As a result, none of hazardous substances (lead, nickel, mercury, cadmium, and arsenic) were detected.

A cream preparation was manufactured using the manufacturing method for fucoidan cosmetic composition according to the present invention. The composition of the cream preparation was as given in the following Table 5.

TABLE 5

| Ingredients | Main functions | Materials | Contents |
|---|---|---|---|
| Purified water | Supplies moisture and functions as another hydrophilic solvent | Ion-exchange water | To 100 |
| Functional extract | Improves wrinkles, skin whitening and moisturization, and relieves inflammation | Adenosine, niacinamide, mozuku extract (5%), Centella extract | ~10% |
| Moisturizer | Helps skin moisturization and supplies moisture | Glycerin, butylene glycol, dipropylene glycol, hyaluronic acid, betaine | ~20% |
| Emulsifier, stabilizer | Makes insoluble ingredients soluble | Cetearyl alcohol, glyceryl monostearate, polysorbate 60, cetearyl olivate, sorbitan olivate, cetyl alcohol, glyceryl stearate, PEG-75 stearate, Ceteth-20, Steareth-20 | ~10% |
| Skin conditioner | Helps skin moisturization, smoothing and regeneration, and relieves inflammation | Macadamia nut oil, capric triglyceride, butylene glycol dicaprylate, camellia seed oil, bee's wax, shear butter, green tea leaf extract, lactobacillus/bean fermentation extract, white willow bark extract, cinnamon bark extract, oregano leaf extract, cypress leaf extract, gold extract, purslane extract | ~20% |
| Natural preservative | Inhibits growth of microorganisms | 1,2-hexadiol | ~2% |
| Thickener | Increases viscosity of aqueous solution | Hydroxyethyl Cellulose acrylate, carbomer | ~0.5% |
| Fragrance | Provides its own fragrant aroma | Fragrance, citronellol, limonene, linalool | ~0.5% |

A skin irritation test of the test substance (cream) was performed on the human body as follows.

Test institution: the Korea Institute of Dermatological Sciences

Test period: Feb. 14, 2020 (test start date)~Mar. 17, 2020 (test end date)

Test subjects: 33 adult male and female volunteers who meet the criteria for selection of test subjects and do not meet the criteria for exclusion.

Test substance: CICA fucoidan cream

Test method: A skin patch test was conducted on 33 subjects using Finn chambers. After wiping the back of each test subject with 70% ethanol and drying it, 20 µL of the test substance was dropped into a 8 mm-diameter disc of the Finn chamber, which was then firmly applied to the test site. The patch was attached to the test site for 24 hours. In 30 minutes, 24 hours, and 48 hours after removal of the patch, a dermatologist observed the degree of skin irritations according to the standards of the ICDRG (International Contract Dermatitis Research Group).

Test results: A patch of "CICA fucoidan cream" commissioned by MS Global Bio Corp., Ltd. was applied to the skin for 24 hours. In 30 minutes, 24 hours, and 48 hours after removal of the patch, the degree of skin irritations occurring on the test site was classified according to the standards of the ICDRG (International Contract Dermatitis Research Group) to determine the mean score of the skin reaction according to the reading criteria for patch tests. There was no skin irritations observed on the test site in 30 minutes, 24 hours, and 48 hours after removal of the "CICA fucoidan cream" patch. It was concluded that no skin irritation occurred according to the mean score of 0.00.

A skin moisturization test of the "CICA fucoidan cream" was performed on the human body as follows.

Test substance: CICA fucoidan cream

Test period: Feb. 10, 2020 (test start date)~Mar. 17, 2020 (test end date)

Test subjects: 21 adult female volunteers 20 years of age or older who meet the criteria for selection of test subjects and do not meet the criteria for exclusion.

Test method: Each volunteer was asked to apply a same amount of the test substance "CICA fucoidan cream" evenly on the face area for absorption after washing the face twice a day for two weeks during the test period.

Evaluation method: The evaluation was conducted in accordance with the standard operating instructions (SOP) of the ICDRG (International Contract Dermatitis Research Group), and all the procedures were checked by the person in charge of the reliability assurance.

In this test, Epsilon E100 (Biox Systems Ltd., UK) was applied to evaluate the skin moisturization effect of the test substance. The moisture content of the skin surface in contact with the sensor of the Epsilon E100 was calculated as an epsilon (ε) value. As the moisture content of the skin increases, the brightness of the image result increases and the blue part changes to white. The same test person measured the skin moisture content in the left cheek area of each subject and analyzed the change in the skin moisture content with Epsilon E100 Software V3.1, an analysis program dedicated to Epsilon E100. It was considered that the skin moisturization was improved when the measured value increased after the use of the test substance. The instrumental measurement was carried out before the use of the test substance, immediately after the one use, and two weeks after the use.

As a result of the skin moisturization evaluation using the Epsilon E100, the skin moisture content was increased by 139.14% immediately after one use of the test substance and 18.42% after weeks of the use, indicating that the skin moisturization improved ($p<0.001$). The test subjects reported that no skin irritation was observed during the test period.

Figure 5:
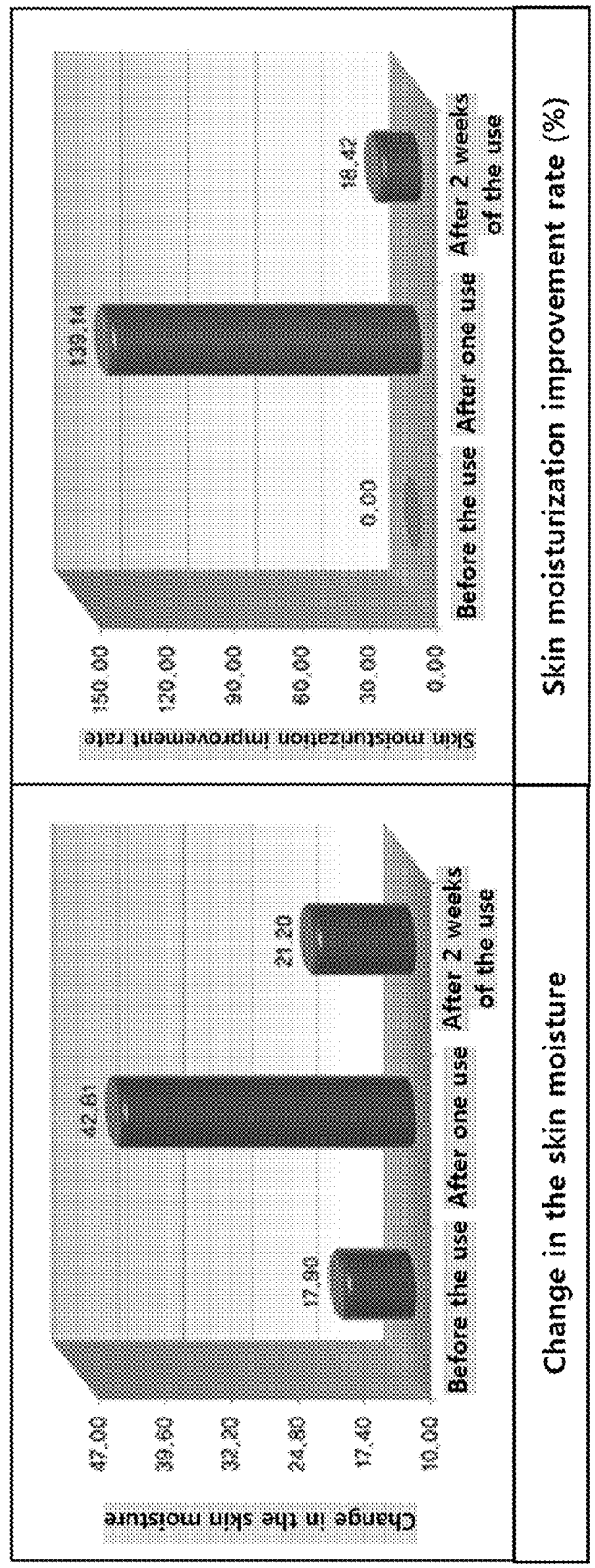
FIG. 5 is a graph showing the evaluation results for skin moisturization before and after the applications of a functional cosmetic containing the low molecular weight fucoidan extract prepared by the present invention.
Figure 6:
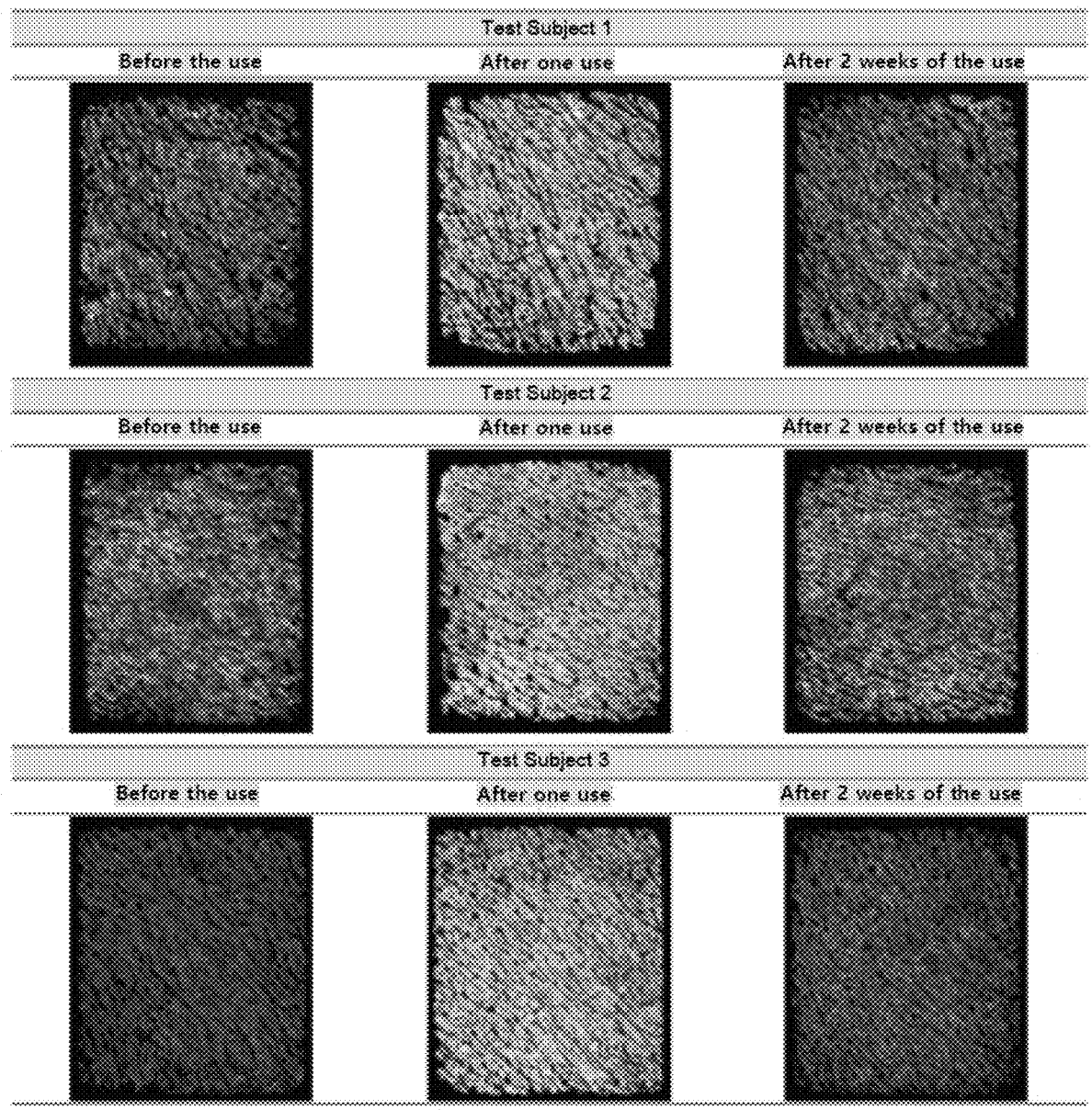
FIG. 6 is an image showing a skin moisturization analysis of the functional cosmetic containing the low molecular weight fucoidan extract prepared by the present invention.

According to the analytical results of the skin moisturization in the left-sided cheek area measured with Epsilon E100, as shown in FIG. 5 and FIG. 6, the skin moisture content was increased by 139.14% immediately after one use of the test substance and 18.42% after two weeks of the use. The change in the skin moisture content immediately after one use of the test substance and after two weeks of the use was considered statistically significant ($p<0.001$), indicating that the test substance helped improve the skin moisturization.

According to the technical solution, the present invention can increase skin moisturization using the hydrophilicity of the sulfate group, which is contained more in fucoidan than in any other brown algae.

Further, the present invention can degrade the molecular weight of fucoidan to a low molecular weight through a fucoidan extraction method and use the low molecular weight fucoidan to significantly increase the absorption of fucoidan as a raw material for cosmetics.

Further, the present invention provides a fomented mozuku extract as a biocompatible material to make an effect of moisturizing the body tissue, wrapping a wound to heal, and preventing inflammation.

Furthermore, the present invention contains fucoidan as a raw material to make an effect of inhibiting the production of IgE, which is the cause of allergic disease manifested by atopic dermatitis or the like, and relieving allergic symptoms.

Like this, it may be understood that the technical construction of the present invention can be implemented into another specific embodiment by those skilled in the art without changing the technical ideas or essential features.

It should be therefore understood that above-described embodiments are illustrative in all respects and not limiting. The scope of the present invention is indicated by the claims rather than the detailed description of the present invention and construed to include all changes and modifications derived from the meanings and scope of the claims and equivalent concepts thereof.

What is claimed is:

1. A method for manufacturing a fucoidan cosmetic composition, comprising:
   (1) washing mozuku to eliminate residual salt and impurities;
   (2) adding citric acid to the washed mozuku and pulverizing the mozuku;
   (3) adding water to the pulverized mozuku and performing reflux extraction to obtain a high molecular weight fucoidan;
   (4) adding a neutralizing agent to the high molecular weight fucoidan for neutralization;
   (5) adding diatomite to the neutralized high molecular weight fucoidan and causing a reaction for 30 minutes for deodorization;
   (6) filtering the deodorized high molecular weight fucoidan to eliminate insoluble substances;
   (7) adding a lactic acid bacterium to the high molecular weight fucoidan removed of the insoluble substances and causing fermentation to degrade the fucoidan to a low molecular weight;
   (8) concentrating the purified low molecular weight fucoidan with a reduced pressure evaporator; and
   (9) powdering the concentrated low molecular weight fucoidan through freeze drying.

2. The method according to claim 1, wherein the reflux extraction of the step (3) is performed at 60 to 100° C. under pressure of 0.1 to 2 kgf/cm$^2$ for 2 to 4 hours.

3. The method according to claim 1, wherein the reflux extraction of the step (3) is performed at pH 2 to 3, the neutralization of the step (4) being performed at pH 6.5 to 7.5.

4. The method according to claim 1, wherein the lactic acid bacterium of the step (7) is at least one selected from the group consisting of *Lactobacillus delbrueckii* subsp. *Lactis* KCTC 3034, *Lactobacillus plantarum* subsp. *Plantarum* KCTC 3107, *Lactobacillus acidophilus* KCTC 3145, *Streptococcus salivarius* subsp. *Thermophiles* KCTC 5098, and *Lactobacillus casei*, the bacterium being added for fermentation.

* * * * *